US00PP18041P3

(12) United States Plant Patent
Gilford

(10) Patent No.: US PP18,041 P3
(45) Date of Patent: Sep. 18, 2007

(54) STRAWBERRY PLANT NAMED 'DRISCOLL BONAIRE'

(50) Latin Name: *Fragaria×ananassa*
Varietal Denomination: Driscoll Bonaire

(75) Inventor: Kristie L. Gilford, Dover, FL (US)

(73) Assignee: Driscoll Strawberry Associates, Inc.

( * ) Notice: Subject to any disclaimer, the term of this patent is extended or adjusted under 35 U.S.C. 154(b) by 13 days.

(21) Appl. No.: 11/244,118

(22) Filed: Oct. 4, 2005

(65) Prior Publication Data

US 2007/0079407 P1 Apr. 5, 2007

(51) Int. Cl.
*A01H 5/00* (2006.01)

(52) U.S. Cl. ..... Plt./209

(58) Field of Classification Search ..... Plt./209, Plt./208

See application file for complete search history.

*Primary Examiner*—Kent Bell
(74) *Attorney, Agent, or Firm*—Jones Day

(57) ABSTRACT

This invention relates to a new and distinct variety of strawberry named 'Driscoll Bonaire'. The variety is similar to the varieties 'Driscoll Malibu' and 'Driscoll Osceola.' The variety is distinguished from 'Driscoll Malibu' and 'Driscoll Osceola,' in particular, by its longer petiole length and wider petiole diameter, longer sepal length and greater sepal width, longer fruit length, greater berry weight and longer harvest interval.

4 Drawing Sheets

Latin name of the genus and species of the plant claimed: The variety is botanically identified as *Fragaria×ananassa.*

Variety denomination: The strawberry variety denomination is 'Driscoll Bonaire'.

BACKGROUND OF THE INVENTION

The new variety originated as a result of a controlled cross between female cultivar 'Driscoll Marathon' (U.S. Plant Pat. No. 12,817) and male cultivar 'Driscoll Madeira' (U.S. Plant Pat. No. 14,109) in an ongoing breeding program, and was discovered as a seedling in Hillsborough County, Fla. in December 2000. The original seedling of the new cultivar was asexually propagated by stolons in a nursery in Shasta County, Calif. Propagules were transplanted to a controlled breeding plot in Hillsborough County, Fla., where the variety was identified and selected for further evaluation. 'Driscoll Bonaire' was subsequently asexually propagated and underwent further testing in Hillsborough County, Fla. for 5 years. This propagation and testing has demonstrated that the combination of traits disclosed herein which characterize the new variety are fixed and retained true to type through successive generations of asexual reproduction.

SUMMARY OF THE INVENTION

The present invention relates to a new and distinct variety of strawberry named 'Driscoll Bonaire.' The variety is botanically identified as *Fragaria×ananassa.* The new variety is distinguished from other varieties by a number of characteristics as set forth in Tables 1–4.

COMPARISON TO SIMILAR VARIETIES

The varieties which we believe to be similar to 'Driscoll Bonaire' from those known to us are 'Driscoll Malibu' (U.S. Plant Pat. No. 16,070) and 'Driscoll Osceola' (U.S. Plant Pat. No 15,752). There are several characteristics of the new variety that are different from, or not possessed by 'Driscoll Malibu' and 'Driscoll Osceola'. For example, the new variety has a longer petiole length and wider petiole diameter, longer sepal length and greater sepal width, longer fruit length, greater berry weight and longer harvest interval. Additional characteristics of Driscoll Bonaire include an orbicular petal shape, a rounded petal apex and an obtuse petal base. The typical and observed petal number of 'Driscoll Bonaire' is five and the petal margin is entire. The typical and observed sepal number of 'Driscoll Bonaire' is ten. 'Driscoll Bonaire' also has a laceolate sepal shape, an acute sepal apex and a serrate sepal margin. 'Driscoll Bonaire' also has a typical and observed broadly orbicular leaflet shape and a round leaflet apex. The typical and observed diameter of the fruiting truss of 'Driscoll Bonaire' is 2.9 and is pale green in color (RHS, 142A). The average number of strawberries on the fruiting truss of 'Driscoll Bonaire' is one. Additionally, the typical and observed length and width of the hollow center of 'Driscoll Bonaire' is 21.7 mm and 7.9 mm respectively. 'Driscoll Bonaire' has a medium sweetness with an average brix of 9.2 and medium acidity with an average brix to acid ratio of 12.18:1.

'Driscoll Bonaire' is distinguished from its reference varieties, 'Driscoll Malibu' and 'Driscoll Osceola' as indicated in Tables 1–4.

The parents, 'Driscoll Marathon' (U.S. Plant Pat. No. 12,817) and 'Driscoll Madeira' (U.S. Plant Pat. No. 14,109), were not available for side by side comparison with 'Driscoll Bonaire'. 'Driscoll Bonaire' differs from 'Driscoll Marathon' by being a less vigorous plant, having much greater flesh firmness and greatly improved skin strength. 'Driscoll Bonaire' differs from 'Driscoll Madeira' by having a much glossier skin and a brighter red color where 'Driscoll Madeira' was a darker red color.

BRIEF DESCRIPTION OF THE DRAWINGS

The accompanying photographs show typical specimens of the new variety, including fruit, foliage and flowers, in color as nearly true as it is reasonably possible to make in color illustrations of these characteristics.

DESCRIPTION OF THE NEW VARIETY

Figure 1:
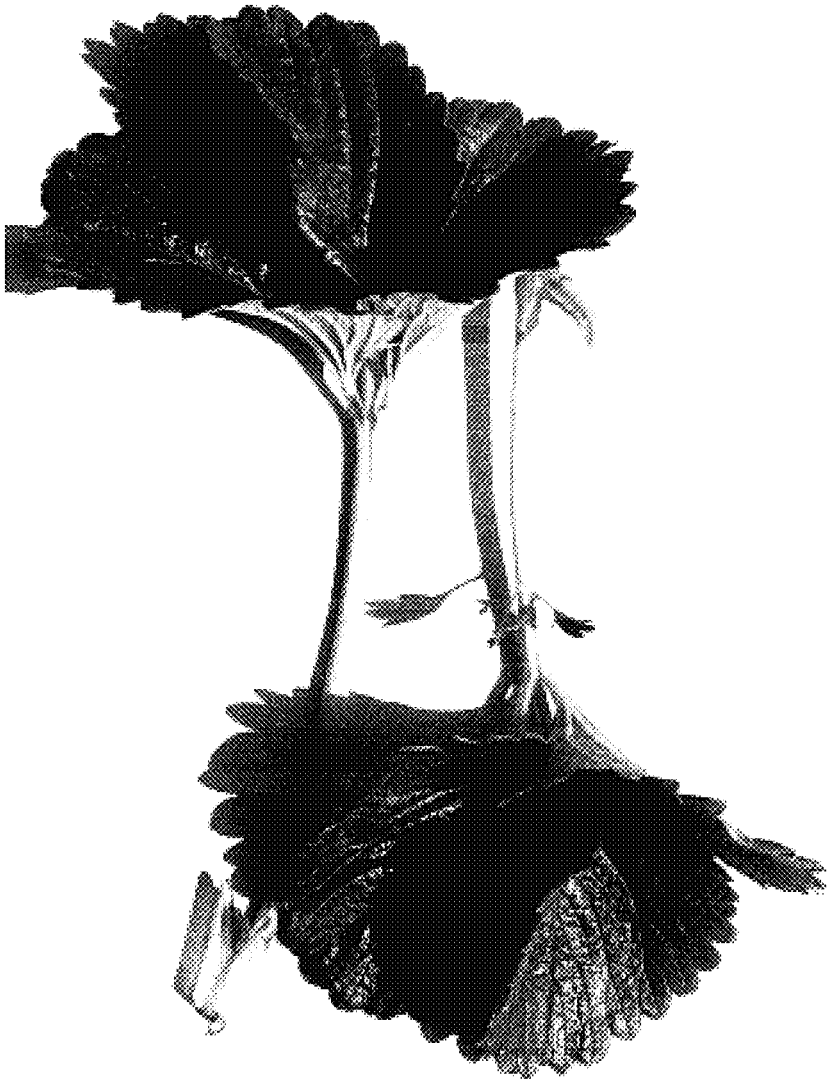
FIG. 1 shows the upper side of the leaves of the plant.
Figure 2:
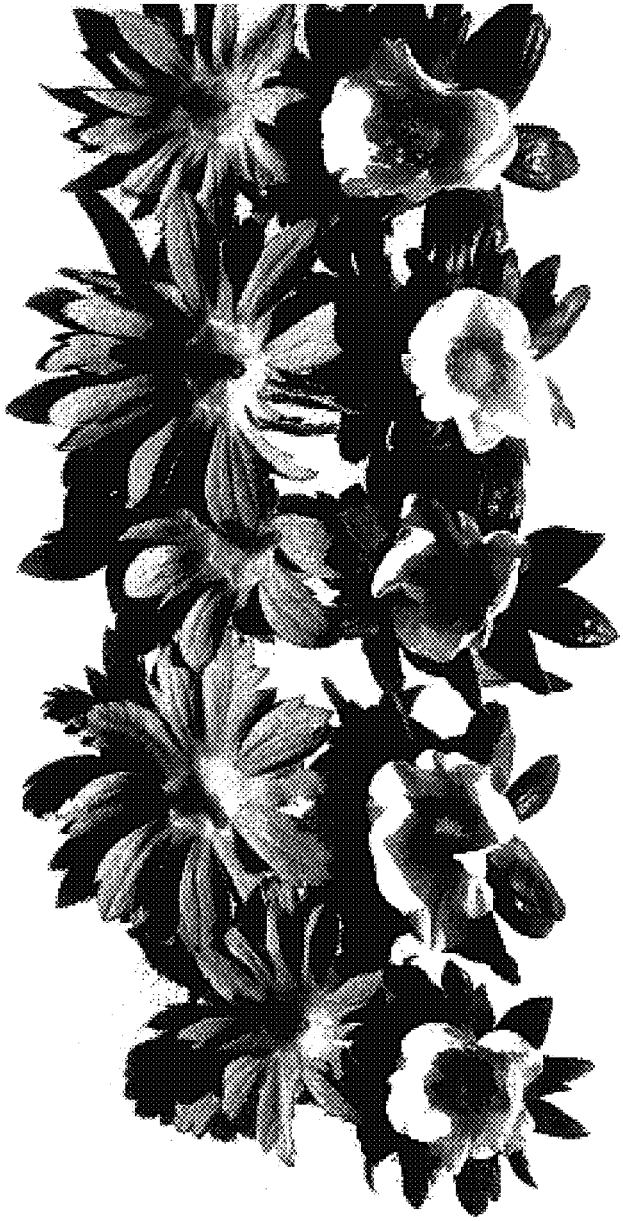
FIG. 2 shows the under side and upper side of the flowers.
Figure 3:
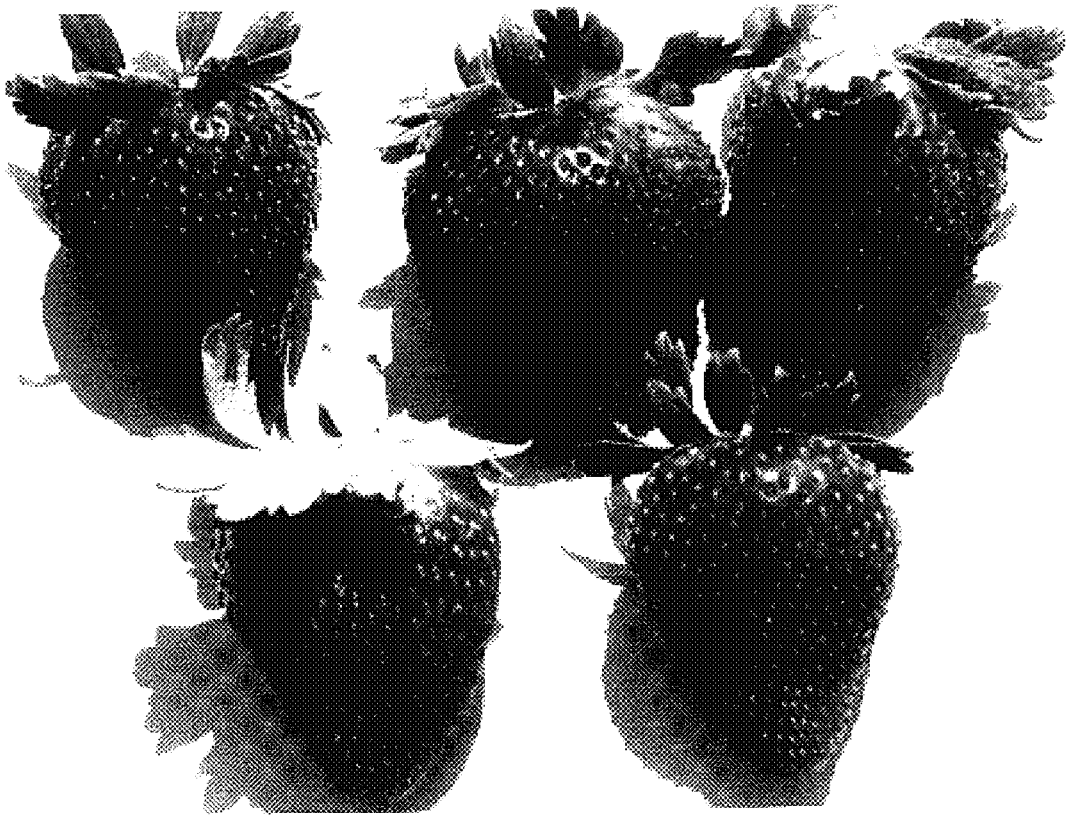
FIG. 3 shows a close-up of the fruit.
Figure 4:
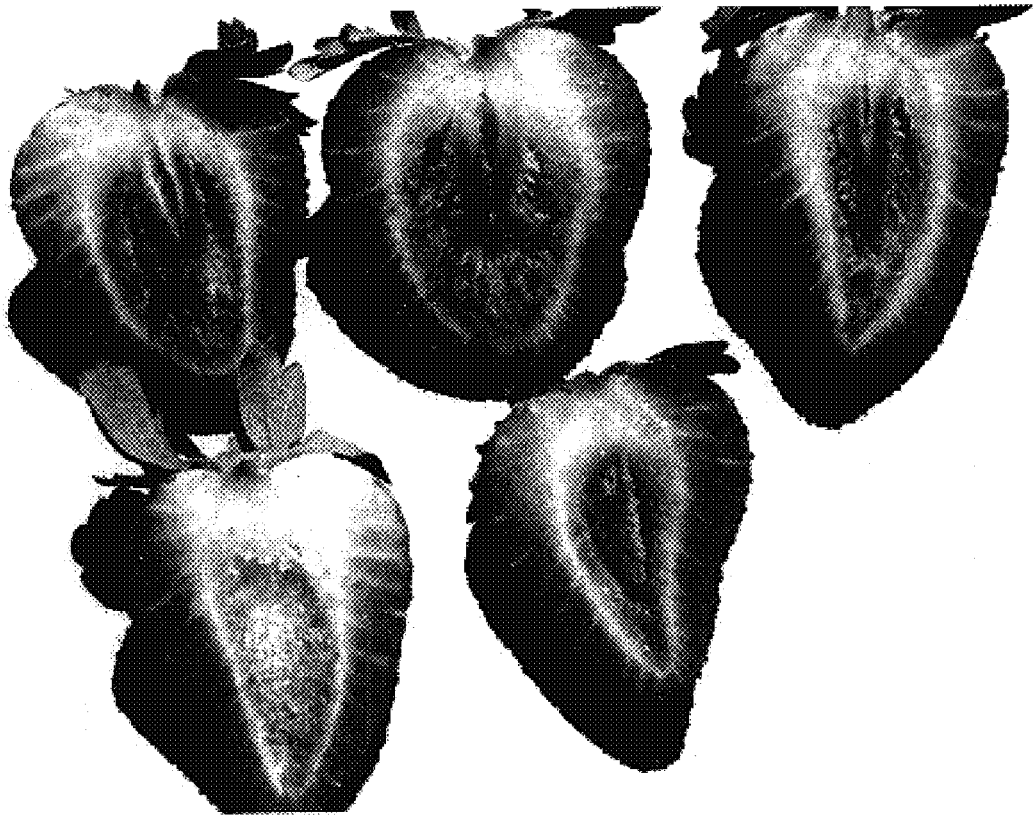
FIG. 4 shows the fruit in longitudinal cross-section.

The following detailed description of the new variety is based upon observations taken of plants harvested from a nursery in McArthur, Calif. in September and October, 2004 and held in cold storage until planting in Hillsborough County, Fla. in October, 2004. Plants were grown in raised beds of soil under conditions typical of commercial strawberry production in Hillsborough County, Fla. Fruits were harvested twice weekly from November, 2004 to April, 2005 for yield determination. Observations of 'Driscoll Bonaire', 'Driscoll Malibu', and 'Driscoll Osceola' were made in side by side comparison in January, 2005. Color designations, color descriptions, and other phenotypical descriptions may deviate from the stated values and descriptions depending upon variation in environmental, seasonal, climatic and cultural conditions. Colors are described and the most similar color designations are provided from The Royal Horticultural Society (R.H.S.) Colour Chart.

PROPAGATION

The new variety is principally propagated by way of stolons. Although propagation by stolons is presently preferred, other known methods of propagating strawberry plants may be employed.

CHARACTERISTICS OF THE NEW VARIETY

Information on the new variety is presented in Tables 1, 2, 3 and 4. In the tables, the flowers described are secondary flowers except where indicated. The fruit described is the secondary fruit on four month old plants. Fruit and flower measurements are an average of both primary and secondary fruit and flowers.

Table 1 provides information on the plant and fruit characteristics of the new variety 'Driscoll Bonaire' compared with characteristics of 'Driscoll Malibu' and 'Driscoll Osceola'. Table 2 provides additional information of the plant and fruit characteristics of the new variety 'Driscoll Bonaire' compared with characteristics of the varieties 'Driscoll Malibu' and 'Driscoll Osceola'. Table 3 provides reactions of the new variety to stresses, pests and diseases compared with reactions of the varieties 'Driscoll Malibu' and 'Driscoll Osceola'. Table 4 provides isozyme characteristics of the new variety as compared to that of the varieties 'Driscoll Malibu' and 'Driscoll Osceola'.

TABLE 1

QUANTITATIVE COMPARISON OF 'DRISCOLL BONAIRE', 'DRISCOLL MALIBU' AND 'DRISCOLL OSCEOLA'

| | 'Driscoll Bonaire' | 'Driscoll Malibu' | 'Driscoll Osceola' |
|---|---|---|---|
| Plant Characteristics | | | |
| Height of Plant (cm) | 9.2 | 11.4 | 8.3 |
| Spread of Plant (cm) | 32.4 | 33.9 | 31.2 |
| Number of Crowns | 3.7 | 4.9 | 3.8 |
| Leaf Characteristics | | | |
| Terminal Leaflet Length (cm) | 7.8 | 6.6 | 6.7 |
| Terminal Leaflet Width (cm) | 7.9 | 6.6 | 8.1 |
| Terminal Leaflet Length/Width Ratio | 0.98 | 0.99 | 0.83 |
| # Teeth/Terminal Leaflet | 25.7 | 22.5 | 23.8 |
| Color of upper side | 132B medium green | 141A light to medium green | 135B medium green |
| Color of under side | 130B light green | 139C light green | 138B light green |
| Petiole Length (cm) | 7.7 | 10.3 | 8.0 |
| Petiole Diameter (mm) | 4.2 | 3.2 | 3.5 |
| Petiole Color | 142C green | 141C green | 140C green |
| Petiolule Length (mm) | 11.2 | 9.8 | 8.3 |
| Petiolule Diameter (mm) | 2.5 | 1.9 | 2.0 |
| Petiolule Color | 142C green | 141C green | 140C green |
| Bract Frequency | 92% typically paired | 83% typically paired | 8% typically single |
| Stipule Length (cm) | 3.07 | 3.46 | 3.53 |
| Stipule Width (cm) | 0.99 | 0.81 | 0.89 |
| Stolon Characteristics | | | |
| Anthocyanin color | 185A greyed purple red | 58A purple red | 59D purple red |
| Diameter at bract (mm) | 3.09 | | |
| Avg. # of Daughter plants (2003 Nursey) | 54 | 55 | 65 |
| Flower Characteristics | | | |
| Petal Length (cm) | 1.40 | 1.22 | 1.38 |
| Petal Width (cm) | 1.52 | 1.29 | 1.48 |
| Petal Length/Width Ratio | 0.92 | 0.95 | 0.93 |
| Flower Diameter (cm) | 2.94 | 2.57 | 2.83 |
| Calyx Diameter (cm) | 4.42 | 3.99 | 4.41 |
| Sepal Length (mm) | 18.3 | 15.6 | 16.9 |
| Sepal Width (cm) | 8.5 | 7.1 | 6.8 |
| Color of Upper Side of Petal | 155C white | 155C white | 155C white |
| Receptical Color | 1B yellow | 1B yellow | 1B yellow |
| Anther Color | 1A yellow | 1A yellow | 1A yellow |
| Fruiting Truss Length (cm) | 13.5 | 14.4 | 11.8 |
| Fruit Characteristics | | | |
| Fruit Length (cm) | 5.2 | 4.7 | 4.2 |
| Fruit Width (cm) | 4.1 | 3.7 | 3.8 |
| Fruit Length/Width Ratio | 1.25 | 1.25 | 1.13 |
| Average Berry Weight (g) | 32.9 | 28.0 | 29.9 |
| External Color | 46A red | 46B red | 46A red |

TABLE 1-continued

QUANTITATIVE COMPARISON OF 'DRISCOLL BONAIRE', 'DRISCOLL MALIBU' AND 'DRISCOLL OSCEOLA'

| | 'Driscoll Bonaire' | 'Driscoll Malibu' | 'Driscoll Osceola' |
|---|---|---|---|
| Internal Color | 43A light red | 48C orange red | 48D orange red |
| Achene Coloration | 178B to 160B Greyed Orange to Greyed Yellow | 178C to 160C Greyed Orange to Greyed Yellow | 178C to 161B Greyed Orange to Greyed Yellow |
| Achenes per berry | 342 | 240 | 225 |
| Achene weight (g) | 0.00058 | 0.00062 | 0.00089 |
| 2004-2005 Marketable Yield (g/plant) | 435 | 333 | 348 |

TABLE 2

QUALITATIVE COMPARISON OF 'DRISCOLL BONAIRE', 'DRISCOLL MALIBU' AND 'DRISCOLL OSCEOLA'

| | 'Driscoll Bonaire' | 'Driscoll Malibu' | 'Driscoll Osceola' |
|---|---|---|---|
| Plant | | | |
| Habit | flat globose | globose | flat globose |
| Canopy Density | medium | medium | open to medium |
| Vigor | medium | weak to medium | medium |
| Leaf | | | |
| Shape in cross section | concave | slightly concave to flat | concave to slightly concave |
| Interveinal blistering | weak | medium | medium |
| Glossiness | medium | weak | medium |
| Number of leaflets | three only | three only | three only |
| Terminal leaflet margin profile | revolute | flat | flat |
| Terminal leaflet shape of base | rounded | rounded | rounded |
| Terminal leaflet shape of teeth | obtuse | obtuse to rounded | obtuse |
| Stipule pubescence | medium | medium | medium |
| Petiole pubescence | dense | dense | dense |
| Petiole pose of hairs | outwards | downwards | outwards to downwards |
| Stolon | | | |
| Anthocyanin coloration | strong | medium to strong | medium to strong |
| Thickness | medium | medium to thick | medium to thick |
| Pubescence | medium | medium | dense |
| Inflorescence | | | |
| Position relative to foliage | level with | level to above | level with to above |
| Diameter of calyx relative to corolla on secondary flowers | larger | larger | larger |
| Diameter of inner calyx relative to outer on secondary flowers | same size | larger | smaller to same size |
| Spacing of petals | overlapping | overlapping | overlapping |
| Fruiting Truss | | | |
| Attitude at first picking | prostrate | prostrate | prostrate |

TABLE 2-continued

QUALITATIVE COMPARISON OF 'DRISCOLL BONAIRE', 'DRISCOLL MALIBU' AND 'DRISCOLL OSCEOLA'

| | 'Driscoll Bonaire' | 'Driscoll Malibu' | 'Driscoll Osceola' |
|---|---|---|---|
| Fruit | | | |
| Predominant shape | conical | conical | conical |
| Difference in shapes between primary and secondary fruits | slight | slight | slight |
| Band without achenes | very narrow | very narrow | very narrow |
| Unevenness of surface | weak | medium | weak |
| Evenness of color | slightly uneven | slightly uneven | slightly uneven |
| Glossiness | strong | strong | strong |
| Insertion of achenes | level with surface | below to level with the surface | below surface |
| Insertion of calyx | level | level | level |
| Pose of the calyx segments | reflexed | reflexed | spreading to reflexed |
| Size of calyx in relation to fruit on secondary fruit | same size to larger | same size to larger | same size to larger |
| Adherence of calyx | strong | strong | strong |
| Firmness of flesh | soft | soft to medium | soft to medium |
| Evenness of flesh color | slightly uneven | slightly uneven | slightly uneven |
| Distribution of flesh color | marginal and central | marginal and central | marginal and central |
| Hollow center size | small | small | medium |
| Sweetness | medium | medium | medium |
| Texture when tasted | fine | medium | fine |
| Acidity | medium | medium | medium |
| Time of First Flowering in 2003 | late October | early November | early November |
| Harvest Interval in 2003 | late November through early April | early December through early April | early December through early April |
| Type of Bearing | partially everbearing | partially everbearing | partially everbearing |

REACTION TO STRESS, PESTS, AND DISEASE

TABLE 3

REACTIONS TO STRESS PESTS AND DISEASES FOR 'DRISCOLL BONAIRE', 'DRISCOLL MALIBU' AND 'DRISCOLL OSCEOLA'

| | 'Driscoll Bonaire' | 'Driscoll El Capitan' | 'Driscoll Venice' |
|---|---|---|---|
| Reaction to Pests | | | |
| *Tetranychus urticae* | susceptible | susceptible | susceptible |
| *Lygus hesperus* | susceptible | susceptible | susceptible |
| Reaction To Diseases | | | |
| *Botrytis* fruit rot | susceptible | susceptible | susceptible |
| Powdery mildew | moderately susceptible | moderately susceptible | moderately susceptible |
| *Verticillium* wilt | susceptible | highly susceptible | highly susceptible |
| Strawberry Mottle Virus | susceptible | susceptible | susceptible |
| *Xanthomonas fragariae* | moderately susceptible | moderately susceptible | moderately susceptible |

ISOZYME ANALYSIS

In addition to the morphological description above, the new cultivar 'Driscoll Bonaire' has been analyzed to obtain an indication of its genetic makeup to provide further means for identifying the new variety and distinguishing it from other somewhat similar and/or related strawberry varieties. Specifically, leaf samples of 'Driscoll Bonaire', 'Driscoll Malibu' and 'Driscoll Osceola' were analyzed by electrophoresis for isozyme patterns of the enzymes phosphoglucoisomerase ("PGI"), leucine aminopeptidase ("LAP") and phosphoglucomutase ("PGM"). See J. Amer. Soc. Hort. Sci. 106:684–687. Isozyme characterization of the three varieties is presented in Table 4, with the letters representing the banding patterns for each enzyme as designated in the above-identified article.

TABLE 4

ISOZYME ANALYSIS FOR 'DRISCOLL BONAIRE', 'DRISCOLL MALIBU' AND 'DRISCOLL OSCEOLA'

| Locus | 'Driscoll Bonaire' | 'Driscoll Malibu' | 'Driscoll Osceola' |
|---|---|---|---|
| PGI | A1 | A1 | A1 |
| LAP | B3 | B3 | B3 |
| PGM | C2 | C4 | C4 |

What is claimed:

1. A new and distinct variety of strawberry plant, substantially as shown and described.

* * * * *